United States Patent
Korodi et al.

(10) Patent No.: US 6,884,888 B2
(45) Date of Patent: Apr. 26, 2005

(54) PROCESS FOR THE PRODUCTION OF N-[3-(3-CYANOPYRAZOLO[1,5-A] PYRIMIDIN-7-YL) PHENYL]-N-ETHYLACETAMIDE (ZALEPLON)

(75) Inventors: Ferenc Korodi, Debrecen (HU); Erika Feher, Debrecen (HU); Erika Magyar, Debrecen (HU)

(73) Assignee: Teva Gyogyszergyar Reszvenytarsasag, Debrecen (HU)

( * ) Notice: Subject to any disclaimer, the term of this patent is extended or adjusted under 35 U.S.C. 154(b) by 0 days.

(21) Appl. No.: 10/170,673

(22) Filed: Jun. 12, 2002

(65) Prior Publication Data

US 2003/0040522 A1 Feb. 27, 2003

Related U.S. Application Data

(60) Provisional application No. 60/297,635, filed on Jun. 12, 2001.

(51) Int. Cl.$^7$ ............................................. C07D 487/04
(52) U.S. Cl. ....................................................... 544/281
(58) Field of Search ......................................... 544/281

(56) References Cited

U.S. PATENT DOCUMENTS 4,626,538 A    12/1986  Dusza et al.
5,714,607 A  *  2/1998  Padmanathan ............... 544/281
6,476,223 B1 * 11/2002  Tombari et al. ............. 544/281
2002/0072527 A1 * 6/2002  Aslam et al. ............. 514/262.1

OTHER PUBLICATIONS

Strobel, "Chemical Instrumentation: A systematic approach, 3$^{rd}$ eidtion" (Wiley, 1989) pp. 381–410, 863–959.*

Snyder "Introduction to Modern Liquid Chromatography, 2$^{nd}$ edition" (Wiley, 1979).*

* cited by examiner

*Primary Examiner*—Mark L. Berch
(74) *Attorney, Agent, or Firm*—Kenyon & Kenyon

(57) ABSTRACT

A process for the production of N-[3-(3-cyanopyrazolo[1,5-a]pyrimidin-7-yl)phenyl]-N-ethylacetamide (zaleplon) that involves reacting N-[3-[3-(dimethylamino)-1-oxo-2-propenyl]phenyl]-N-ethylacetamide or a salt thereof with 3-amino-4-cyanopyrazole or a salt thereof under acidic conditions in a reaction medium comprising a mixture of water and a water-miscible organic compound produces zaleplon in high yield and high purity. A regioisomer of zaleplon (N-[3-(3-cyanopyrazolo[1,5-a]pyrimidin-5-yl)phenyl]-N-ethylacetamide) is useful as a reference standard for monitoring the composition of production batches of zaleplon.

24 Claims, 2 Drawing Sheets

HPLC CHROMATOGRAM OF ZALEPLON MADE BY THE METHOD OF THE PRESENT INVENTION

HPLC CHROMATOGRAM OF REGIOISOMER

PROCESS FOR THE PRODUCTION OF N-[3-(3-CYANOPYRAZOLO[1,5-A] PYRIMIDIN-7-YL) PHENYL]-N-ETHYLACETAMIDE (ZALEPLON)

CROSS-REFERENCE TO RELATED APPLICATIONS

This application claims the benefit of provisional application Ser. No. 60/297,635, filed Jun. 12, 2001.

FIELD OF THE INVENTION

The present invention relates to an improved process for producing N-[3-(3-cyanopyrazolo[1,5-a]pyrimidin-7-yl)phenyl]-N-ethylacetamide.

BACKGROUND OF THE INVENTION

Zaleplon, whose systematic chemical name is N-[3-(3-cyanopyrazolo[1,5-a]pyrimidin-7-yl)phenyl]-N-ethylacetamide, possesses anxiolytic, antiepileptic, sedative and hypnotic properties. It is approved by the U.S. Food and Drug Administration for short-term treatment of insomnia.

Zaleplon and a process for preparing it are disclosed in U.S. Pat. No. 4,626,538, which is incorporated herein by reference. In the '538 patent process, shown in Scheme 1, N-(3-acetylphenyl)ethanamide is condensed with dimethylformamide dimethyl acetal to form N-[3-[3-(dimethylamino)-1-oxo-2-propenyl)]phenyl]acetamide. The primary amide of the acetamide is then alkylated with ethyl iodide, forming N-[3-[3-(dimethylamino)-1-oxo-2-propenyl]phenyl]-N-ethylacetamide 1. To prepare zaleplon in the last step, ethylacetamide 1 is condensed with 3-amino-4-cyanopyrazole 2 by refluxing the reactants in glacial acetic acid for eight hours.

Scheme 1

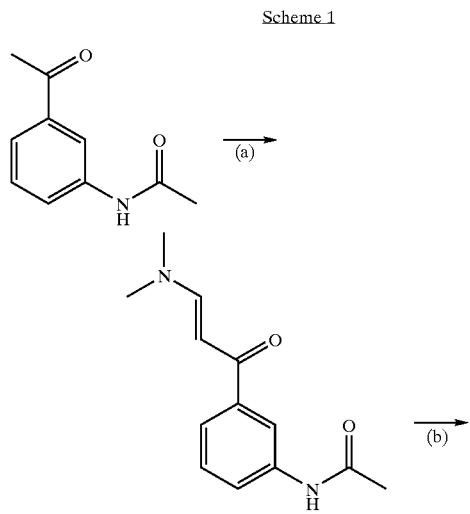

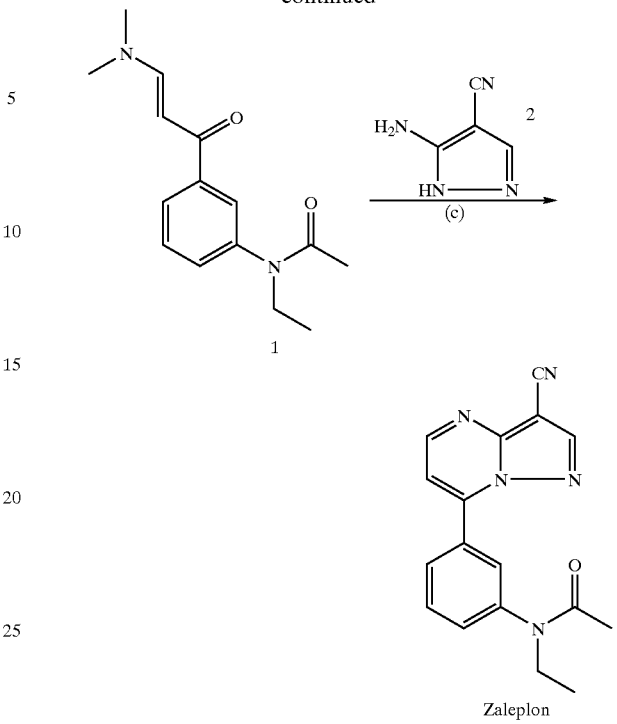

(a) dimethylformamide dimethyl acetal, refl.;
(b) ethyl iodide, sodium hydride, DMF;
(c) glacial acetic acid, refl.

U.S. Pat. No. 5,714,607 discloses an improvement upon the '538 patent process. According to the '607 patent, zaleplon can be obtained in improved yield and purity if the final step of the '538 patent process is modified by adding water to the acetic acid solvent at about 10% to about 85% (v/v). It is also reported that the reaction is faster when water is added. As stated in the '607 patent, the improved conditions shorten the reaction time from about 3–3.5 to about 1–3.5 hours. According to Table 1 of the '607 patent, zaleplon was obtained in yields ranging from 81.7–90% and in HPLC purity ranging from 98.77 to 99.4%.

Nevertheless, development of a more advantageous procedure for production of zaleplon under acidic conditions starting from ethylacetamide and 3-amino-4-cyanopyrazole in high yield and purity and in a short time is still desirable.

In order to obtain marketing approval for a new drug product, manufacturers have to submit to the regulatory authorities evidence to show that the product is acceptable for human administration. Such a submission must include, among other things, analytical data to show the impurity profile of the product to demonstrate that the impurities are absent, or are present only a negligible amount. For such a demonstration there is a need for analytical methods capable of detection of the impurities and reference markers for identification and assaying thereof.

SUMMARY OF THE INVENTION

The present invention provides a process for producing zaleplon by reacting N-[3-[3-(dimethylamino)-1-oxo-2-propenyl]phenyl]-N-ethylacetamide and 3-amino-4-cyanopyrazole in a liquid reaction medium of water and a water-miscible organic compound under acidic conditions. The reaction proceeds through an imine intermediate that is prone to precipitate from water. The imine intermediate remains dissolved in the reaction media of this invention.

The process proceeds rapidly at ambient temperature to produce highly pure zaleplon in high yield. The process is suitable for small or large-scale production of pure zaleplon.

In another embodiment, the present invention relates to pure zaleplon having a purity, as determined by HPLC, of at least 98.5%.

In yet another aspect, the present invention relates to pure zaleplon having a purity of at least 99% as determined by HPLC.

In another aspect, the present invention relates a method for preparation of a novel chemical compound, N-[3-(3-cyanopyrazolo[1,5-a]pyrimidin-5-yl)phenyl]-N-ethylacetamide, which is the regioisomer and main process impurity of zaleplon. This new compound, which is characterized by NMR and MS investigations, can be used as a reference marker in analysis of zaleplon.

In still a further aspect, the present invention relates to analytical methods for testing and show the impurity profile of zaleplon. These methods are also suitable for analyzing and assaying zaleplon and its main impurity which, in the methods of the invention, serves as reference marker.

DETAILED DESCRIPTION OF THE INVENTION

Figure 1:
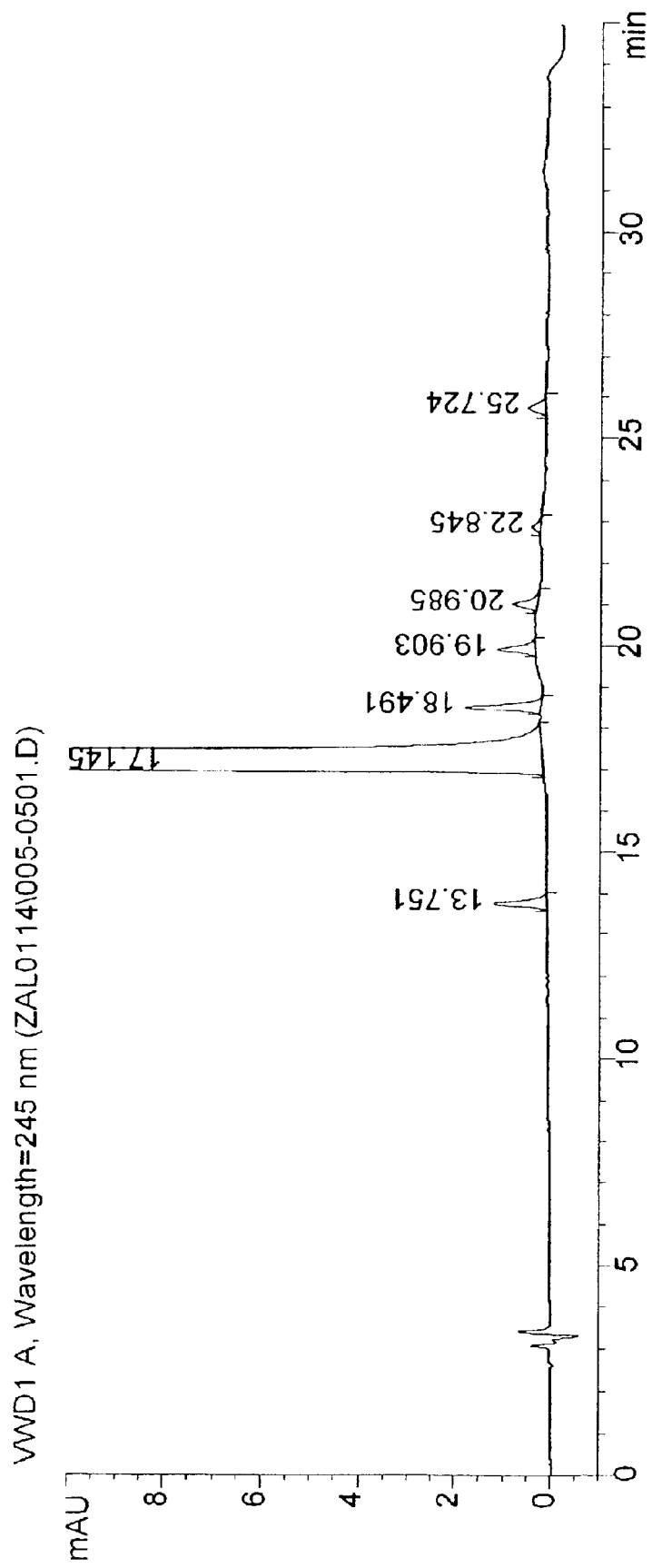
FIG. 1 shows a typical HPLC chromatogram for zaleplon produced by the method of the present invention.
Figure 2:
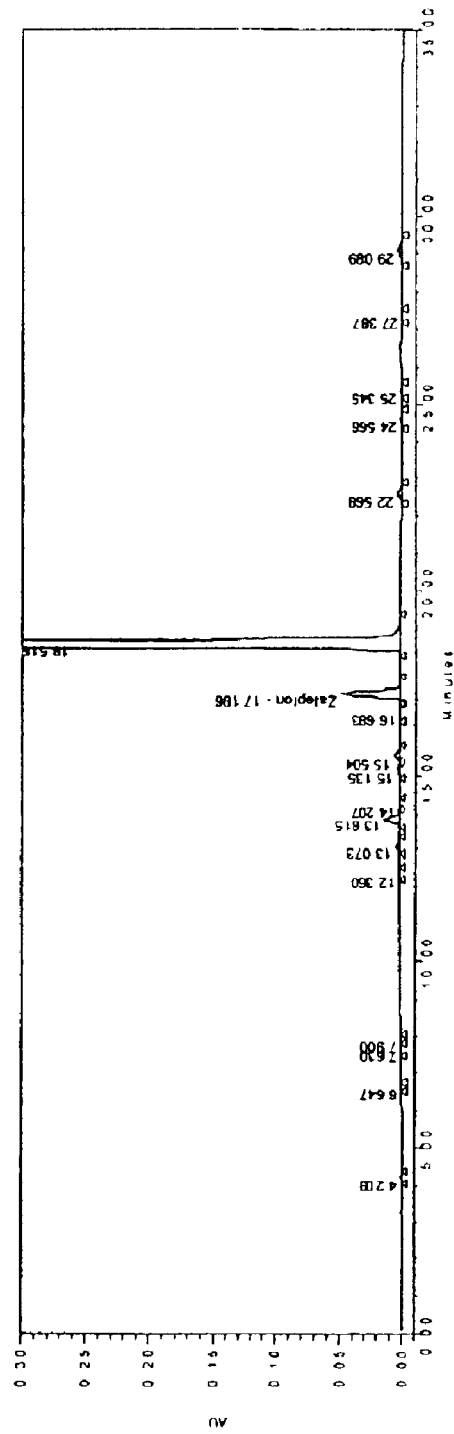
FIG. 2 shows the HPLC chromatogram of the novel compound N-[3-(3-cyanopyrazolo[1,5-a]pyrimidin-5-yl)phenyl]-N-ethylacetamide produced by the method of the present invention.

The present invention is based on a mechanistic study and new observations concerning the reaction of N-[3-[3-(dimethylamino)-1-oxo-2-propenyl]phenyl]-N-ethylacetamide 1 with 3-amino-4-cyanopyrazole 2 leading to zaleplon. Our observations include identification of a reaction intermediate, imine 3 by high performance liquid chromatography-mass spectroscopy. Our results, including the identification of the imine intermediate, are consistent with a reaction mechanism that is set forth in Scheme 2.

Scheme 2

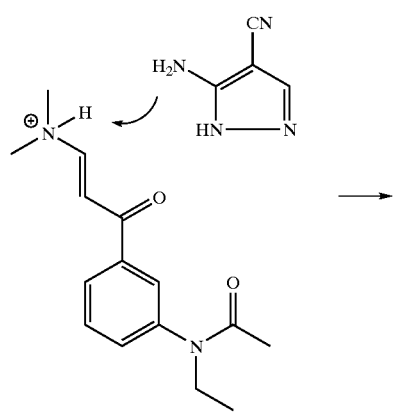

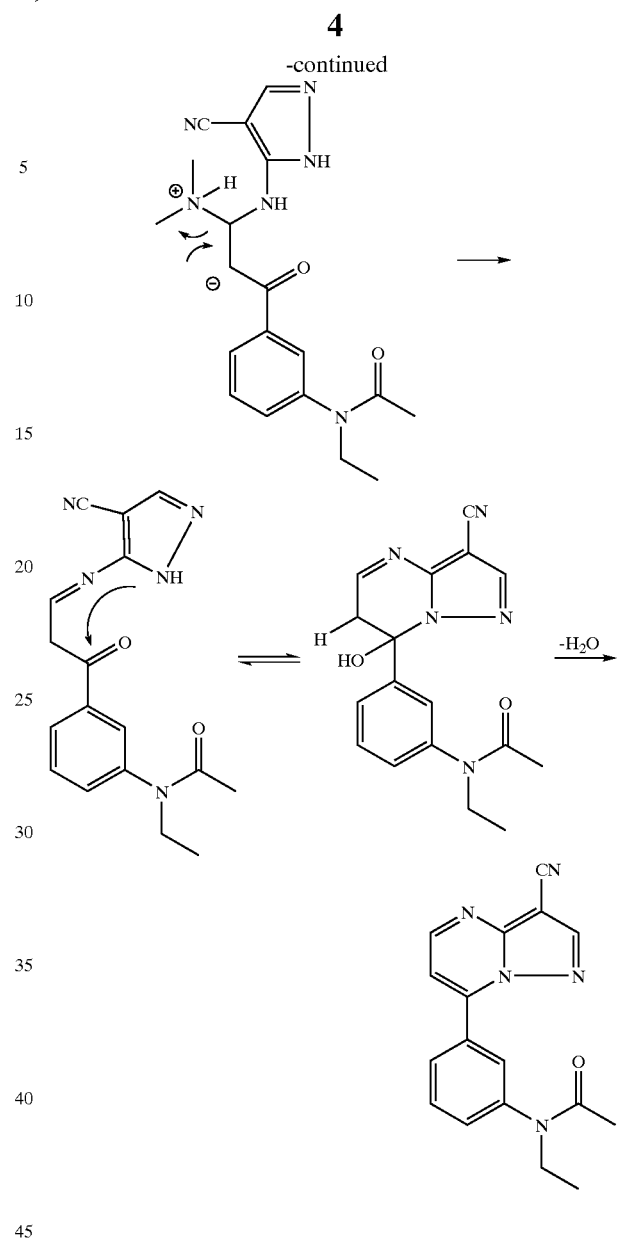

According to Scheme 2, ethylacetamide 1 undergoes Michael-type addition of the 3-amino group of pyrazole 2. α-Elimination of dimethylamine from a transient charge-separated intermediate restores the double bond, which rearranges to form imine intermediate 3. The 2-nitrogen atom of the pyrazole ring cyclizes onto the keto group with elimination of water forming zaleplon.

Both the addition and cyclization reactions occur in the presence of acid. The dimethylamine liberated in the first elimination step binds an equivalent of acid. Consequently an excess of acid is required for this sequence of acid catalyzed conversions to go to completion.

The starting materials, imine intermediate, and product have significantly different polarities. It became apparent during the course of our study that while aqueous mineral acid is a good solvent for both starting materials 1 and 2, it is not a good solvent for imine intermediate 3 or zaleplon. Imine intermediate 3 tends to separate from aqueous mineral acids that do not contain a significant amount of a water-miscible organic co-solvent and forms an oily precipitate, thereby preventing the reaction from going to completion.

The starting materials and imine intermediate are soluble in a variety of protic and polar aprotic organic solvents. Unfortunately, the rate of the reaction is solvent dependent and is much slower in the organic solvents we tried than it is in water.

Overcoming the above-mentioned solubility problems, the present invention provides a process for producing zaleplon whereby ethylacetamide 1, or an acid addition salt thereof, is reacted with 3-amino-4-cyanopyrazole 2, or an acid addition salt thereof, in a reaction medium of water and at least one water-miscible organic compound in the presence of an acid. The quantity of water, organic solvent, and acid can be adjusted independently. The water-miscible organic solvent can tend to solubilize imine intermediate 3. As stated previously, an equivalent or more of an acid must be present in order to maintain acidic conditions throughout the course of the reaction. By including at least one water-miscible organic compound, the solvating power in the reaction medium is decoupled from the choice of acid. This flexibility is advantageous because it enables optimization of the production process simultaneously for yield and reaction rate. Such flexibility is not possible in prior art processes. In the process described in the '607 patent, varying the amount of acid is the only means of altering the solvating properties of the reaction medium.

In particular, the reaction medium for production of zaleplon from compounds 1 and 2 according to this invention is a mixture of water and at least one water-miscible organic solvent (organic co-solvent). Organic co-solvents suitable in the practice of the present invention include organic compounds that do not bear carboxylic acid groups, such as $C_1$–$C_6$ monohydroxyl and polyhydroxyl alcohols (e.g. methanol, ethanol, propanol), nitriles (e.g. acetonitrile, propionitrile), ethers (e.g. tetrahydrofuran, dioxane), nitro compounds (e.g. nitromethane, nitroethane), amides (e.g. formamide, dimethylformamide, acetamide, dimethylacetamide, hexamethylphosphoramide and hexamethylphosphortriamide, sulfoxides (e.g. dimethylsulfoxide), and other water-miscible organic compounds that are inert to the reagents and/or the product. Any of the above recited co-solvents can be used alone, or any of them can be used in any combination.

The ratio of organic co-solvent to water in the reaction medium is preferably from about 10% to about 90% (v/v) organic co-solvent in water, more preferably from about 30% to about 40% (v/v) organic co-solvent in water. Most preferably, the reaction medium is a mixture of about 36% (v/v) methanol in water.

As used herein in connection with the composition of water and organic co-solvent in a reaction medium, volume % (vol-%), % v/v, and N% v/v (where N is a number from 1 up to and including 100) are synonymous and calculated as follows (illustrated for species A):

$$\text{Vol-}\%_A = Wt_A \times \rho_A / (Wt_A \times \rho_A + Wt_B \times \rho_B)$$

where:

$Wt_A$ and $Wt_B$ are the weights in grams of species A and B, respectively, and $\rho_A$ and $\rho_B$ are the densities, in g./ml. of species A and B, respectively.

Suitable acids for use in the practice of the method of the present invention include inorganic acids, such as hydrochloric acid, hydrobromic acid, sulfuric acid, phosphoric acid and boric acid, and water-miscible organic acids, such as formic acid, acetic acid, propionic acid, oxalic acid, malonic acid and tartaric acid. The acid should be used in at least an amount capable of protonating all of the liberated dimethylamine, thereby maintaining an at least moderately acidic environment for ring closure of imine intermediate 3 and completion of the zaleplon-forming reaction. An acid may be added individually as such to the reaction mixture. Alternatively, the acid may be added as the proton donating component of an acid addition salt of ethylacetamide 1 or pyrazole 2. Thus, it will be appreciated by those skilled in the art that up to about two equivalents of acid may be added by using acid addition salts of the starting materials. Therefore, separate individual addition of an acid as such is not strictly necessary to establish acidic conditions.

Preferred acids include hydrochloric acid and phosphoric acid, either of which is preferably present in the reaction mixture in an amount of from about one to about two molar equivalents with respect to the limiting reagent. Starting materials 1 and 2 may be used in any ratio. The one present in the lesser molar amount constitutes the limiting reagent to which the amount of acid should be compared. The starting materials are preferably used in approximately equimolar amounts due to their cost.

In accord with especially preferred sets of production parameters used in Examples 1, 3–5, 13, 14, 19 and 20, the reaction goes to completion within several hours at ambient temperature, without external heating or cooling. The process according to the present invention is preferably conducted at a temperature in the range of from about 20° C. to about 25° C. The reaction also may be conducted at elevated temperature, up to the boiling point of the reaction medium (e.g. Examples 16–18), as well as at lower temperatures (e.g. Example 21).

The reaction time necessary for complete conversion is about 2 to about 8 hours at a temperature in the range of from about 20° C. to about 25° C., depending upon the composition of the reaction mixture. The time required for the reaction to go to completion may be decreased to about 0.2 hours at an elevated temperature of about 50° C. Reactions performed with cooling require more time to reach completion (about 6 to about 8 hours) but yield a product of somewhat higher purity (compare Examples 13 and 21).

By following the preferred embodiments of the invention, the zaleplon product precipitates from the reaction mixture by the end of the reaction or may be induced to precipitate by cooling. The precipitate may be recovered by filtration. Cooling the reaction mixture before collecting the product may increase the yield.

This process produces pure N-[3-(3-cyanopyrazolo[1,5-a]pyrimidin-7-yl)phenyl]-N-ethylacetamide (zaleplon) in the highest yield currently reported. The process of this invention achieves a higher reaction rate at lower temperatures than is possible using known processes for producing zaleplon.

The purity of the product, as isolated, is very high (above 98.5%). However, if desired, pure zaleplon obtained by the process of the present invention and having a purity of at least 98.5%, preferably at least 99%, as determined by HPLC, can be recrystallized from a solvent, preferably from methanol, ethanol, or a reaction medium of water and a co-solvent such as methanol, ethanol, acetonitrile and the like in order to produce a drug substance that complies with regulatory requirements.

Formation of N-[3-(3-cyanopyrazolo[1,5-a]pyrimidin-5-yl)phenyl]-N-ethylacetamide (4), regioisomer of zaleplon, has been discovered as a main impurity in the synthesis of zaleplon starting from 3-amino-4-cyanopyrazole and N-[3-[3-(dimethylamino)-1-oxo-2-propenyl]phenyl]-N-ethylacetamide. The amount of this impurity has been found to be strongly dependent on the reaction conditions.

According to the reaction conditions claimed in the U.S. Prov. Pat. Appl. 60/297635 the amount of this impurity is in the range of 0.2–0.5% (HPLC) in the crude product.

In another embodiment the present invention provides a method for the preparation of the novel N-[3-(3-cyanopyrazolo[1,5-a]pyrimidin-5-yl)phenyl]-N-ethylacetamide (4) starting from 3-amino-4-cyanopyrazole and N-[3-[3-(dimethylamino)-1-oxo-2-propenyl]phenyl]-N-ethylacetamide by reacting them in water or in the mixture of water and a water miscible organic solvent in the presence of an acid. The amount of this impurity can be increase by up to 5% (HPLC) be use of a high concentration of a strong acid. This facilitates the isolation and characterization of this new compound.

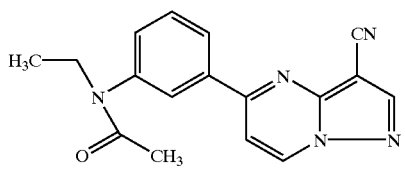

4

The reaction can be performed at 20° to 30° C. or at higher temperature up to the boiling point of water. A temperature of 20° to 30° C. is preferred. As a water miscible organic solvent both polar protic (acetic acid, methanol, ethanol i-propanol) or aprotic (acetonitrile, tetrahydrofuran, dimethylformamide) solvents be applied. As an acid, both mineral (hydrochloric, sulfuric, phosphoric) and organic (acetic, trifluoroacetic, methanesulfonic) can be used. Hydrochloric acid is the preferred acid.

In a preferred embodiment of the present invention the reaction is performed in water in the presence of hydrochloric acid at about 25° C. The isolation of the mixture of zaleplon and its regioisomer 4 can be performed by evaporation, filtration, extraction and by combination of this methods.

In a particularly preferred embodiment of the present invention, after completion of the reaction, the reaction mixture is diluted with water and the precipitated zaleplon is removed by filtration. Then the filtrate is neutralized to precipitate the mixture of zaleplon and its regioisomer 4. A further crop of the mixture can be obtained by extraction of water phase with water inmiscible organic solvents such as ethylacetate, dichloromethane, chloroform and like.

Isolation of compound 4 can be performed by chromatography Column chromatography, preparative TLC or HPLC can be applied. Column chromatography is preferred. As a packing, silica gel or aluminium oxide can be used. Silica gel is preferred. As an eluent, different organic solvents or mixtures of them can be used. Mixtures of dichloromethane and acetone are preferred. The isolated 2 was characterized with $^1$H-nmr and $^{13}$C-nmr spectroscopic as well as mass spectrometric investigations to prove its structure.

In a further embodiment, the present invention provides novel HPLC methods for determination of the impurity profile and assay of zaleplon.

In one such embodiment, suitable for complete resolution (separation) of the peak of zaleplon (1) from the peak of structurally very similar compound (4) as well as the other impurities, the present invention provides a method for HPLC including the steps of:

a, dissolving zaleplon sample in acetonitrile:water (1:1) diluent, b, injecting the sample solution onto an RP-18, 5 μm, HPLC column, c, gradient eluting with a mixture of ammonium-formate buffer and acetonitrile, and d, measuring of the amounts of each impurity at 245 nm wavelength with a UV detector and appropriate recording device.

In another embodiment, particularly suitable for analysis and assay of zaleplon and its main impurity 4 in a drug substance and pharmaceutical compositions containing zaleplon, the present invention provides an HPLC method including the steps of:

a, dissolving zaleplon sample in acetonitrile:water (1:1) diluent, b, injecting the sample solution onto an RP-18, 3 μm, HPLC column, c, eluting the sample from the column using mixture of ammonium-format buffer and acetonitrile with determined flow rate, and d, measuring the zaleplon content of the relevant sample at 245 nm wavelength with a UV detector and appropriate recording apparatus.

Having thus described the various aspects of the present invention, the following non-limiting examples are provided to illustrate specific embodiments.

EXAMPLES

Example 1

N-[3-[3-(dimethylamino)-1-oxo-2-propenyl]phenyl]-N-ethylacetamide (2.6 g, 0.01 mol) and 3-amino-4-cyanopyrazole (1.08 g, 0.01 mol) were dissolved in the mixture of water (35 cm$^3$) and methanol (20 cm$^3$). Phosphoric acid (85%) (0.67 cm$^3$, 0.01 mol) was then added and the mixture was stirred at room temperature for about 4 hours. The reaction mixture was then cooled to about 5° C. and the crystalline product that formed was collected, washed with water and dried at about 60° C. to yield zaleplon (2.79 g, 91.5%) in 98.83% purity as determined by HPLC.

Example 2

N-[3-[3-(dimethylamino)-1-oxo-2-propenyl]phenyl]-N-ethylacetamide (2.6 g, 0.01 mol) and 3-amino-4-cyanopyrazole (1.08 g, 0.01 mol) were dissolved in the mixture of water (35 cm$^3$) and ethanol (20 cm$^3$). Phosphoric acid (85%) (0.67 cm$^3$, 0.01 mol) was then added and the mixture was stirred at room temperature for about 8 hours. The reaction mixture was then cooled to about 5° C. and the crystalline product that formed was collected, washed with water and dried at about 60° C. to yield zaleplon (2.95 g, 96.7%) in 99.09% purity as determined by HPLC.

Example 3

N-[3-[3-(dimethylamino)-1-oxo-2-propenyl]phenyl]-N-ethylacetamide (2.6 g, 0.01 mol) and 3-amino-4-cyanopyrazole (1.08 g, 0.01 mol) were dissolved in the mixture of water (35 cm$^3$) and methanol (20 cm$^3$). Concentrated (37%) hydrochloride acid (1.0 cm$^3$, 0.012 mol) was then added and the mixture was stirred at room temperature for about 2 hours. The reaction mixture was then cooled to about 5° C. and the crystalline product that formed was collected, washed with water and dried at about 60° C. to yield zaleplon (2.80 g, 91.8%) in 98.69% purity as determined by HPLC.

The effects of different reaction conditions are illustrated in Table 1

TABLE 1

| Ex. | Moles of ethylacetamide 1 | Temp. (C.) | Volume of Water (cm³) | Co-solvent Co-solvent | Co-solvent Volume (cm³) | Acid Acid | Acid Moles | Acid Equivalents | Time (h) | Yield (%) | Purity[a] (%) |
|---|---|---|---|---|---|---|---|---|---|---|---|
| 4  | 0.01 | 23 | 35 | MeOH | 20 | $H_3PO_4$ | 0.015 | 1.5 | 4    | 94.5 | 98.82 |
| 5  | 0.01 | 23 | 35 | MeOH | 20 | $H_3PO_4$ | 0.020 | 2   | 4    | 93.0 | 98.80 |
| 6  | 0.01 | 23 | 15 | MeOH | 40 | $H_3PO_4$ | 0.015 | 1.5 | 36   | 90.0 | 99.40 |
| 7  | 0.01 | 23 | —  | MeOH | 55 | $H_3PO_4$ | 0.015 | 1.5 | >72  | —    | —     |
| 8  | 0.01 | 23 | 35 | EtOH | 14 | $H_3PO_4$ | 0.015 | 1.5 | 8    | 96.1 | 98.40 |
| 9  | 0.01 | 23 | 35 | DMF  | 20 | $H_3PO_4$ | 0.015 | 1.5 | 10   | 87.9 | 98.57 |
| 10 | 0.01 | 23 | 35 | ACN  | 20 | $H_3PO_4$ | 0.015 | 1.5 | 20   | 78.2 | 99.74 |
| 11 | 0.01 | 23 | 35 | THF  | 20 | $H_3PO_4$ | 0.015 | 1.5 | 72   | 89.2 | 98.40 |
| 12 | 0.01 | 23 | 35 | MeOH | 20 | HCl       | 0.010 | 1.0 | 24   | 82.0 | 98.95 |
| 13 | 0.01 | 23 | 35 | MeOH | 20 | HCl       | 0.015 | 1.5 | 2    | 92.1 | 98.91 |
| 14 | 0.01 | 23 | 35 | MeOH | 20 | HCl       | 0.020 | 2.0 | 2    | 95.1 | 99.12 |
| 15 | 0.01 | 23 | 35 | —    | —  | AcOH      | 0.260 | 26  | 5    | 85.0 | 98.97 |
| 16 | 0.01 | 50 | 35 | MeOH | 20 | $H_3PO_4$ | 0.015 | 1.5 | 0.25 | 90.2 | 99.25 |
| 17 | 0.01 | 50 | 35 | MeOH | 20 | HCl       | 0.015 | 1.5 | 0.2  | 88.9 | 99.16 |
| 18 | 0.01 | 65 | —  | MeOH | 55 | $H_3PO_4$ | 0.015 | 1.5 | 16   | 79.0 | 98.71 |

[a]Determined as percent area of the peak corresponding to zaleplon in an HPLC chromatogram of the crude reaction mixture

Example 19

N-[3-[3-(dimethylamino)-1-oxo-2-propenyl]phenyl]-N-ethylacetamide (26.0 g, 0.1 mol) and 3-amino-4-cyanopyrazole (10.8 g, 0.1 mol) were dissolved in the mixture of water (350 cm³) and methanol (200 cm³). Concentrated (37%) hydrochloric acid (12.5 cm³, 0.12 mol) was then added and the mixture was stirred at room temperature for about 2 hours. The reaction mixture was then cooled to about 5° C. and the crystalline product formed was collected, washed with water and dried at about 60° C. to yield zaleplon (29.8 g, 97.7%) in 99.08% purity as determined by HPLC.

Example 20

N-[3-[3-(dimethylamino)-1-oxo-2-propenyl]phenyl]-N-ethylacetamide (2.6 g, 0.01 mol) and 3-amino-4-cyanopyrazole-hydrochloride (1.44 g, 0.01 mol) were dissolved in the mixture of water (35 cm³) and methanol (20 cm³). Concentrated (37%) hydrochloric acid (0.83 cm³, 0.01 mol) was then added and the mixture was stirred at room temperature for about 2 hours. The reaction mixture was then cooled to about 5° C. and the crystalline product formed was collected, washed with water and dried at about 60° C. to yield zaleplon (2.93 g, 96.1%) in 99.16% purity as determined by HPLC.

Example 21

N-[3-[3-(dimethylamino)-1-oxo-2-propenyl]phenyl]-N-ethylacetamide (2.6 g, 0.01 mol) and 3-amino-4-cyanopyrazole (1.08 g, 0.01 mol) were dissolved in the mixture of water (35 cm³) and methanol (20 cm³). Concentrated (37%) hydrochloric acid (1.25 cm³, 0.015 mol) was then added and the mixture was stirred at about 15° C. for about 8 hours. The reaction mixture was then cooled to about 5° C. and the crystalline product formed was collected, washed with water and dried at about 60° C. to yield zaleplon (2.87 g, 94.1%) in 99.5% purity as determined by HPLC.

Example 22

Preparation of N-[3-(3-cyanopyrazolo[1,5-a] pyrimidin-5-yl)phenyl]-N-ethyl-acetamide N-[3-[3-(dimethylamino)-1-oxo-2-propenyl]phenyl]-N-ethylacetamide (5.2 g, 0.02 mol) and 3-amino-4-cyanopyrazole (2.16 g, 0.02 mol) were dissolved in the mixture of water (50 ml) and concentrated hydrochloric acid (40 ml) and the mixture was stirred at room temperature for 8 h. The reaction mixture was then cooled to 5° C. and the precipitate was removed by filtration. The filtrate was neutralized by concentrated aqueous ammonia solution to precipitate 380 mg of the mixture of zaleplon and its regioisomer 4 which was collected by filtration. The filtrate was extracted with 100 ml of ethylacetate to give 100 mg of the mixture of the above two compounds upon evaporation. The two crops combined were put to a silica gel column (100 g) and the elution was performed by the solvent mixture of chloroform and acetone 3:1 (v/v) to yield as a second crop 240 mg (4%) of 4; mp 194–196° C.; $^1$H-NMR (CDCl$_3$) δ (ppm) 1.143 (t, 3H), 1.876 (s, 3H), 3.804 (q, 2H), 7.361 (d, 1H), 7.532 (d, 1H), 7.613 (t, 1H), 8.018 (s, 1H), 8.159 (d, 1H), 8.375 (s, 1H), 8.805 ((d, 1H); $^{13}$C-NMR (CDCl$_3$) δ (ppm) 12.89, 22.68, 43.84, 83.17, 107.71, 112.84, 127.17, 127.48, 130.62, 131.63, 136.67, 137.46, 144.10, 148.31, 149.99, 158.60, 169.90; MS (EI, 70 EV) m/z (%) 305 (M$^+$, 18), 248 (59).

We claim:

1. A process for producing zaleplon comprising:
   a.) providing a mixture of N-[3-[3-(dimethylamino)-1-oxo-2-propenyl]phenyl]-N-ethylacetamide and 3-amino-4-cyanopyrazole in a liquid reaction medium of water and at least one water-miscible organic compound free of carboxylic acid groups, wherein the at least one water-miscible organic compound is selected from the group consisting of $C_1$–$C_6$ alcohols, nitriles, ethers, nitro compounds, and sulfoxides,
   b.) forming zaleplon under acidic conditions via an intermediate that is soluble in the reaction medium, and
   c.) recovering zaleplon from the reaction medium.

2. The process according to claim 1 where the water-miscible organic compound is selected from the group consisting of methanol, ethanol, propanol, acetonitrile, propionitrile, tetrahydrofuran, dioxane, nitromethane, nitroethane, and dimethylsulfoxide.

3. The process according to claim 1 wherein the reaction medium contains from about 10% to about 90% (v/v) of at least one water-miscible organic compound in water.

4. The process according to claim 3 wherein the reaction medium contains from about 30% to about 40% (v/v) of at least one water-miscible organic compound in water.

5. The process according to claim 1 wherein the solution contains an acid selected from the group consisting of inorganic acids and water-miscible organic acids.

6. The process according to claim 5 wherein the acid is an inorganic acid.

7. The process according to claim 6 wherein the inorganic acid is selected from the group consisting of hydrochloric acid, hydrobromic acid, sulfuric acid, phosphoric acid and boric acid.

8. The process according to claim 5 wherein the acid is a water-miscible organic acid.

9. The process according to claim 8 wherein the water-miscible organic acid is selected from the group consisting of formic acid, acetic acid, propionic acid, oxalic acid, malonic acid, and tartaric acid.

10. The process according to claim 5 wherein the acid is present in at least 1 molar equivalent with respect to whichever of N-[3-[3-(dimethylamino)-1-oxo-2-propenyl]phenyl]-N-ethylacetamide and 3-amino-4-cyanopyrazole is present in lesser molar quantity.

11. The process according to claim 5 wherein providing the mixture comprises adding an acid addition salt of N-[3-[3-(dimethylamino)-1-oxo-2-propenyl]phenyl]-N-ethylacetamide to the reaction medium.

12. The process according to claim 11 wherein the acid and the acid of the N-[3-[3-(dimethylamino)-1-oxo-2-propenyl]phenyl]-N-ethylacetamide acid addition salt are the same.

13. The process according to claim 5 wherein providing the mixture comprises adding an acid addition salt of 3-amino-4-cyanopyrazole to the reaction medium.

14. The process according to claim 13 wherein the acid and the acid of the 3-amino-4-cyanopyrazole acid addition salt are the same.

15. The process according to claim 1 wherein the zaleplon is formed at a temperature of from about 10° C. to about 100° C.

16. The process according to claim 15 wherein the temperature is from about 20° C. to about 25° C.

17. The process according to claim 1 wherein the zaleplon is recovered in about 0.2 hours to about 8 hours after providing the mixture.

18. The process according to claim 17 wherein the zaleplon is recovered in about 2 hours to about 4 hours after providing the mixture.

19. The process according to claim 1 wherein zaleplon precipitates from the reaction medium and is recovered by separating the reaction medium and dissolved substances from the precipitate.

20. The process according to claim 5 wherein the reaction medium is about 30% to about 40% (v/v) methanol in water, the acid is hydrochloric acid, and the hydrochloric acid is used in an amount of from about 1 to about 2 molar equivalents with respect to whichever of N-[3-[3-(dimethylamino)-1-oxo-2-propenyl]phenyl]-N-ethylacetamide and 3-amino-4-cyanopyrazole is present in lesser molar quantity.

21. The process according to claim 19 wherein zaleplon is formed at a temperature of from about 20° C. to about 25° C. and is recovered about 2 to about 4 hours after providing the mixture.

22. The process according to claim 5 wherein the reaction medium is about 30% to about 40% (v/v) methanol in water, the acid is phosphoric acid, and the phosphoric acid is used in an amount of about 1 to about 2 molar equivalents with respect to whichever of N-[3-[3-(dimethylamino)-1-oxo-2-propenyl]phenyl]-N-ethylacetamide and 3-amino-4-cyanopyrazole is present in lesser molar quantity.

23. The process according to claim 22 wherein zaleplon is formed at temperature of from about 20° C. to about 25° C. and recovered in about 2 to about 4 hours after providing the mixture.

24. The process according to claim 1 wherein the at least one water-miscible organic compound is selected from the group consisting of $C_1$–$C_6$ alcohols, nitriles, ethers, nitro compounds and sulfoxides.

* * * * *